US008855741B2

(12) United States Patent
Shih et al.

(10) Patent No.: US 8,855,741 B2
(45) Date of Patent: Oct. 7, 2014

(54) METHOD AND APPARATUS FOR ACQUIRING AN IMAGE BIOMARKER AND PROGNOSING A BLOOD RELATED DISEASE

(75) Inventors: Tiffany Ting-Fang Shih, Taipei (TW); Timothy K. Shih, Taipei (TW)

(73) Assignee: National Taiwan University, Taipei (TW)

( * ) Notice: Subject to any disclaimer, the term of this patent is extended or adjusted under 35 U.S.C. 154(b) by 1111 days.

(21) Appl. No.: 12/711,089

(22) Filed: Feb. 23, 2010

(65) Prior Publication Data

US 2011/0066024 A1   Mar. 17, 2011

(30) Foreign Application Priority Data

Sep. 17, 2009 (TW) .............................. 98131362 A

(51) Int. Cl.
*A61B 5/05* (2006.01)
*G06T 7/00* (2006.01)
*A61B 5/055* (2006.01)
*G06F 19/00* (2011.01)
*G01R 33/56* (2006.01)

(52) U.S. Cl.
CPC ..... *G06T 7/0014* (2013.01); *G06T 2207/10096* (2013.01); *G01R 33/5601* (2013.01); *A61B 5/055* (2013.01); *G06T 2207/20081* (2013.01); *G06F 19/321* (2013.01); *G06F 19/3431* (2013.01); *G06T 2207/30104* (2013.01); *G06T 2207/30096* (2013.01); *G06F 19/345* (2013.01)
USPC ........... 600/411; 600/407; 600/410; 600/416; 600/419; 600/420

(58) Field of Classification Search
CPC ............................ A61B 5/055; G01R 33/5601
USPC ................. 600/407, 410, 411, 416, 419, 420
See application file for complete search history.

(56) References Cited

PUBLICATIONS

"Functional MR imaging of tumor angiogenesis predicts outcome of patients with acute myeloid leukemia" by Shih et al. Leukemia. 20. pp. 357-362. 2006.*
"Multiple Biomarkers for the Prediction of First Major Cardiovascular Events and Death" by T.J. Wang et al. New England Journal of Medicine. 355. pp. 2631-2639. 2006.*
"Analysis of Myocardial Perfusion MRI" by M. Jerosch-Herold et al. J Magnetic Resonance Imaging. 19. pp. 758-770. 2004.*
"Estimating Kinetic Parameters from Dynamic Contrast-Enhanced T1-Weighted MRI of a Diffusable Tracer: Standardized Quantities and Symbols" by P.S. Tofts et al. J Magnetic Resonance Imaging. 10. pp. 223-232. 1999.*
"Pharmacokinetic Parameters in CNS Gd-DTPA Enhanced MR Imaging" by G. Brix et al. J Computer Assisted Tomography. 15(4). pp. 621-628. 1991.*

* cited by examiner

*Primary Examiner* — Tse Chen
*Assistant Examiner* — Jason Ip
(74) *Attorney, Agent, or Firm* — Hannah M. Tien

(57) ABSTRACT

A method of acquiring an image biomarker suitable for prognosis of a blood-related disease, such as acute myeloid leukemia, includes the steps of: (a) acquiring physical parameter sets, each including at least two parameters, respectively from time-signal intensity curves, these curves being respectively obtained from magnetic resonance image sets of different subjects; each of the image sets being acquired through MRI scanning using one of first and second configuration parameter sets; (b) analyzing the physical parameter sets thus acquired and (c) establishing a risk score function that is a sum of products of each of the physical parameters and the corresponding weight value, wherein a risk score obtained using the risk score function serves as the image biomarker suitable for prognosis of the blood-related disease.

19 Claims, 13 Drawing Sheets

INITIAL DIAGNOSIS

METHOD AND APPARATUS FOR ACQUIRING AN IMAGE BIOMARKER AND PROGNOSING A BLOOD RELATED DISEASE

CROSS-REFERENCE TO RELATED APPLICATION

This application claims priority of Taiwanese Application No. 098131362, filed on Sep. 17, 2009.

BACKGROUND OF THE INVENTION

1. Field of the Invention

The present invention relates to a method of prognosis, more particularly to a method of prognosis of a blood-related disease or hematological malignancy using a magnetic resonance imaging (MRI) scanner.

2. Description of the Related Art

Recently, it is well recognized that development and progression of cancer is related to angiogenesis. Hence, it is possible to predict progression of cancer (e.g., bone marrow-related malignancy, such as acute myeloid leukemia) by evaluating abnormality of angiogenesis.

Conventional follow-ups of patients under treatment for leukemia require the patients to undergo bone marrow biopsy on a regular basis so as to evaluate recovery of the patients. However, in the process of bone marrow biopsy, the patients have to endure pain, and hence bone marrow biopsy cannot be repeated within a short duration of time. Furthermore, data of angiogenesis obtained by bone marrow biopsy is static and is limited to the area of the bone marrow biopsy specimen, and thus cannot be used for observing real-time in vivo vascular perfusion and changes in permeability. Therefore, the monitoring of therapeutic outcome of leukemia is limited.

To address this issue, Shih T. T. et al. proposed in "Functional MR Imaging of Tumor Angiogenesis Predicts Outcome of Patients with Acute Myeloid Leukemia", Leukemia 2006; 20(2):357-62, a method of prognosis of acute myeloid leukemia using a MRI scanner. This method performs a training procedure with a group of patients so as to determine a cutoff point for categorizing the patients into one of a high-risk group and a low-risk group. The cutoff point is further used for evaluation of angiogenesis and prognosis of leukemia. As shown in FIG. 1, the training procedure includes six consecutive steps.

In Step 1-1, a patient is injected with a contrast agent while the patient is scanned using a MRI scanner (the MRI scanning starts 10 seconds before the patient is injected with the contrast agent, and then the injection and the scanning continue concurrently), that is configured according to a configuration parameter set, so as to acquire a magnetic resonance (MR) image set of the patient.

In Step 1-2, for each image of the MR image set, a region of interest (ROI) is selected, and an intensity value of the ROI is obtained as a sum of pixel values of all pixels in the ROI. A time-signal intensity curve is subsequently plotted using the intensity values of the images in the MR image set.

In Step 1-3, a physical parameter is acquired from the time-signal intensity curve. The physical parameter can be a peak enhancement ratio or an initial maximum enhancement slope.

In Step 1-4, Step 1-1 to Step 1-3 are repeated with different patients to acquire different physical parameters. It is to be noted that the same contrast agent and MRI scanner configuration parameter set are used in this step.

In Step 1-5, the physical parameters of the different patients are analyzed using classification and regression tree (CART) techniques with reference to conditions of the patients so as to acquire a cutoff point of the physical parameter. The cutoff point categorizes the patients into one of a high-risk group and a low-risk group. The patients in the high risk-group have a higher angiogenesis rate and a poorer prognosis, which means the patients have a lower overall survival (OS) and a lower disease-free survival (DFS) compared to the patients in the low-risk group.

After completion of the above-mentioned training procedure, a prognosis of a patient with leukemia can be obtained by comparing the physical parameter of the patient (acquired through Step 1-1 to Step 1-3) with the cutoff point (acquired in Step 1-5). According to the physical parameter and the cutoff point, the patient is categorized into one of the high-risk group and the low-risk group, and evaluation of angiogenesis and prognosis of leukemia can be evaluated therefrom. It is to be noted that in the prognosis, it is mandatory to use the MRI scanner and the configuration parameter set used in the training process. Preferably, the same contrast agent is used in the prognosis.

The method proposed by Shih T. T. et al. uses dynamic contrast-enhancement magnetic resonance imaging (DCE-MRI), which is fast, non-invasive, permits repeated measurement within a short duration of time, and determines a specific cutoff point. Nevertheless, the cutoff point is suitable for use only if the MRI scanner and the configuration parameter set used for deriving the cutoff point are used. If other hospitals use another MRI scanner or configuration parameter set, the cutoff point cannot be used and the same process needs to be repeated for a certain amount of patients followed by subsequent analysis of the cutoff points. This is because the physical parameter obtained in the training procedure and the cutoff point derived therefrom are based on a particular model of the MRI scanner and a particular configuration parameter set. Therefore, if a different MRI scanner or a different configuration parameter set is used, it is necessary to perform the training procedure so as to determine a corresponding cutoff point. In addition, if a different contrast agent is used, the training procedure needs to be performed so as to acquire a corresponding cutoff point.

SUMMARY OF THE INVENTION

Therefore, an object of the present invention is to provide a method of acquiring an image biomarker that is applicable to different models of MRI scanners and different configuration parameter sets.

Accordingly, a method of the present invention for acquiring an image biomarker suitable for prognosis of a blood-related disease, such as acute myeloid leukemia, includes the steps of:

a) using an analyzing unit to acquire physical parameter sets, each including at least two physical parameters, respectively from time-signal intensity curves, the time-signal intensity curves being respectively obtained from magnetic resonance image sets of different subjects that are diagnosed as having the blood-related disease, each of the magnetic resonance image sets being acquired through magnetic resonance imaging (MRI) scanning using one of first and second configuration parameter sets;

b) using a parameter significance-evaluating unit to analyze the physical parameter sets thus acquired with reference to prognoses of the different subjects so as to evaluate significance of each of the physical parameters and obtain weight values corresponding to the physical parameters; and c) configuring a computing unit to establish a risk score function that is a sum of products of each of the physical parameters and the corresponding weight value, wherein a risk score obtained using the risk score function serves as the image biomarker suitable for prognosis of the blood-related disease.

Another object of the present invention is to provide a method, device, and computer program product that use the image biomarker for prognosis of a blood-related disease.

Accordingly, a method of the present invention for prognosis of a blood-related disease includes the steps of:

i) using an analyzing unit to acquire a physical parameter set, that includes at least two physical parameters, from a time-signal intensity curve, the time-signal intensity curve being obtained from a magnetic resonance image set of a patient suspected of having the blood-related disease;

ii) using a computing unit to compute a risk score of the patient based on a risk score function established in the computing unit and the physical parameters acquired by the analyzing unit, the risk score function being a sum of products of each of the physical parameters and a weight value corresponding thereto; and iii) using a risk-evaluating unit to evaluate and predict a condition of the patient based on the computed risk score.

An apparatus of the present invention for prognosis of a blood-related disease is adapted to process a magnetic resonance image set of a patient acquired using a magnetic resonance imaging (MRI) scanner. The apparatus includes:

an image processing unit for processing the magnetic resonance image set to obtain a time-signal intensity curve;

an analyzing unit for acquiring a physical parameter set, that includes at least two physical parameters, from the time-signal intensity curve obtained by the image processing unit;

a computing unit for computing a risk score of the patient based on a risk score function established in the computing unit and the physical parameters acquired by the analyzing unit, the risk score function being a sum of products of each of the physical parameters and a weight value thereof; and a risk-evaluating unit for evaluating and predicting a condition of the patient based on the risk score computed by the computing unit.

A computer program product of the present invention includes a machine-readable storage medium that includes program instructions for causing a computer to perform consecutive steps of a method of prognosis of a blood-related disease. The program instructions include:

a first code for configuring the computer to receive and process a magnetic resonance image set of a patient acquired using a magnetic resonance imaging (MRI) scanner to obtain a time-signal intensity curve;

a second code for configuring the computer to acquire a physical parameter set, that includes at least two physical parameters, from the time-signal intensity curve;

a third code for configuring the computer to compute a risk score of the patient based on a pre-established risk score function and the physical parameters acquired from the time-signal intensity curve, the risk score function being a sum of products of each of the physical parameters and a weight value corresponding thereto; and a fourth code for configuring the computer to evaluate and predict a condition of the patient based on the computed risk score.

BRIEF DESCRIPTION OF THE DRAWINGS

Other features and advantages of the present invention will become apparent in the following detailed description of the preferred embodiment with reference to the accompanying drawings, of which:

FIG. 8($b$) is a plot of survival rates of the 78 patients during the follow-up;

FIG. 8($c$) is a diagram showing the peak, amplitude, and K trans parameters of the 78 patients;

FIG. 9($b$) shows plots of disease-free survival rate of each of the high- and low-risk groups, respectively;

DETAILED DESCRIPTION OF THE PREFERRED EMBODIMENT

The preferred embodiment of a method of prognosis of a blood-related disease (such as acute myeloid leukemia) according to the present invention includes a training phase and an application stage.

Figure 1:
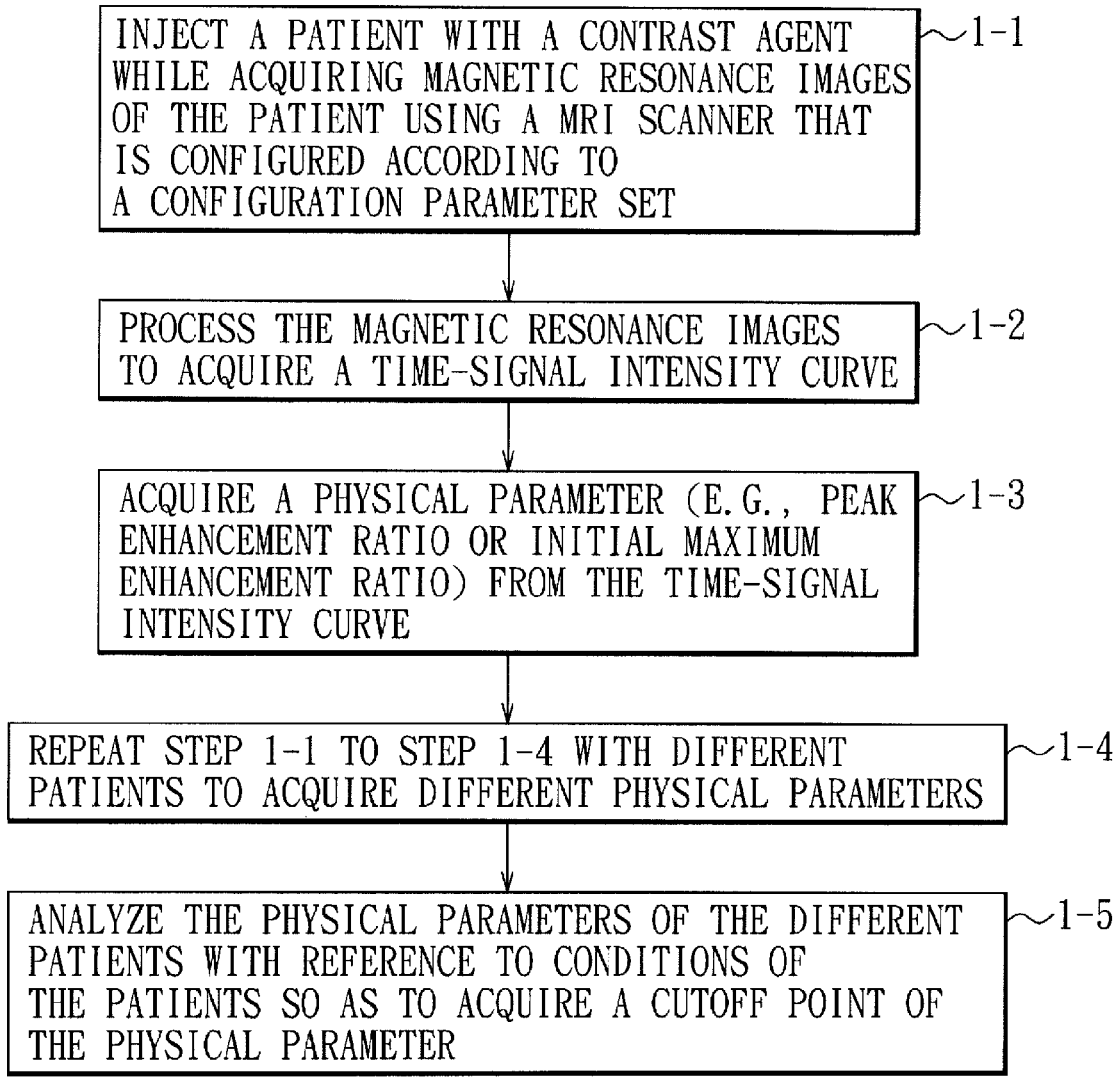
FIG. 1 is a flow chart illustrating a conventional training procedure for acquiring a physical parameter and a cutoff point.
Figure 2:
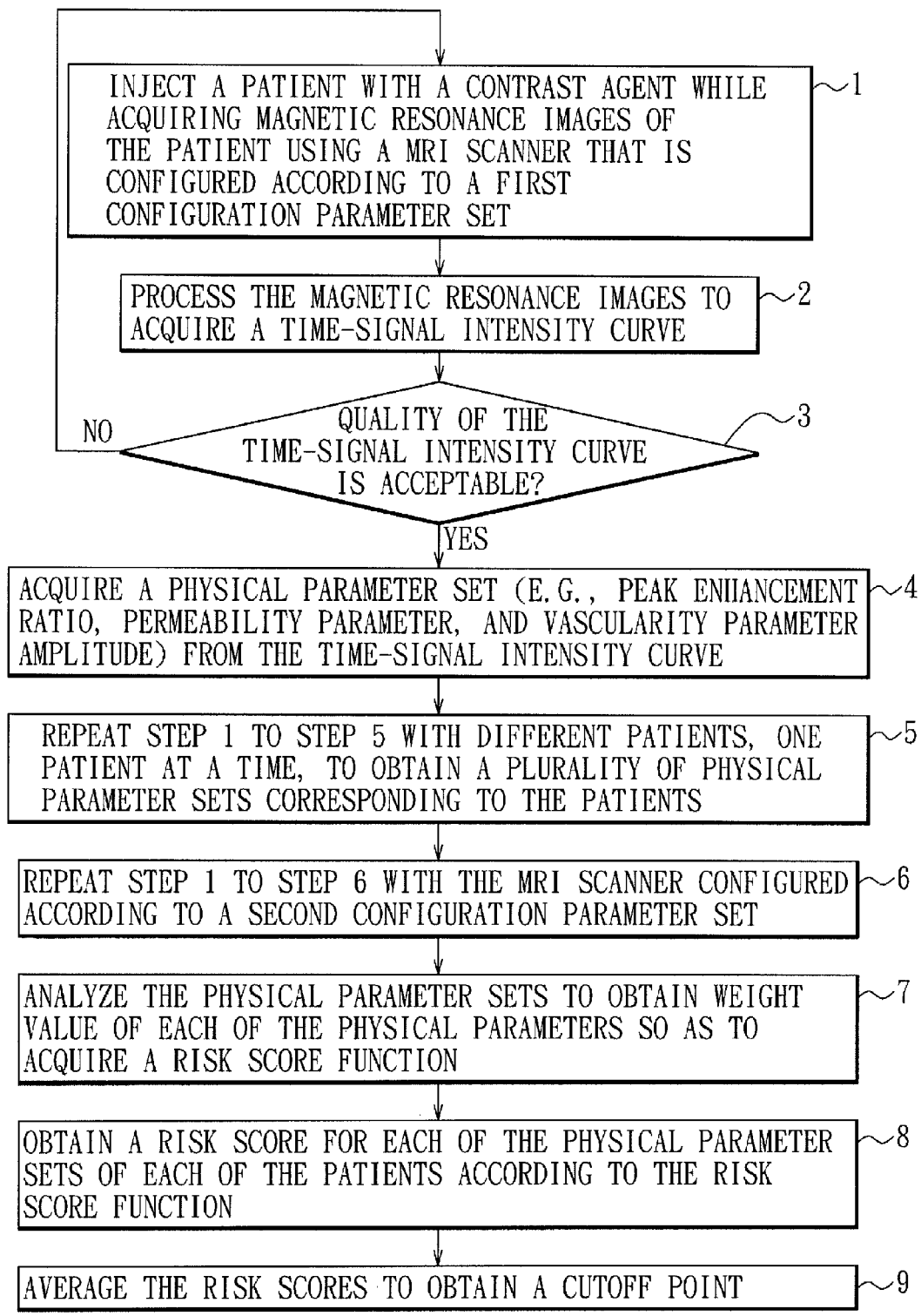
FIG. 2 is a flow chart illustrating the preferred embodiment of a method of the present invention suitable for acquiring physical parameters and a corresponding cutoff point of a blood-related disease.

Training Phase:

The purpose of the training phase is to acquire an image biomarker suitable for prognosis of a blood-related disease. Referring to FIG. 2, below are the steps of the training phase.

In Step 1, a patient is injected with a contrast agent while the patient is scanned using a MRI scanner (the MRI scanning starts 10 seconds before the patient is injected with the contrast agent, and then the injection and the scanning continue concurrently) that is configured according to a first configuration parameter set so as to acquire a magnetic resonance (MR) image set containing a plurality of consecutive MR images of the patient. The MRI scanner used in the training phase can be of any model. The first configuration parameter set includes: pulse sequences, field of view, slice thickness, repetition time, echo time, pre-pulse inversion time, flip angle, bandwidth, acquisition matrix, average of excitation, acquisition rate, and acquisition time. Each of the listed parameters has a range of adequate parameter values, and the parameters are adjusted according to injection speed of the contrast agent and biological characteristics of scanned regions (e.g., rate of blood flow or characteristics of microcirculation). For example, if rate of blood flow and permeability at the scanned region are faster, injection speed of the contrast agent and acquisition rate of the MRI scanner need to be faster; and slower if otherwise.

In Step 2, for each image of the MR image set, a region of interest (ROI) is selected, and a corresponding signal intensity value of the ROI is obtained as a sum of pixel values of all pixel values in the ROI. A time-signal intensity curve is subsequently plotted according to the signal intensity values and the corresponding times of scanning of the MR images.

In Step 3, quality of the time-signal intensity curve is evaluated using a quality-evaluating unit: if quality of the time-signal intensity curve is not acceptable, the flow goes back to Step 1 with adjustments made to the first configuration parameter set. The present embodiment refers to "Analysis of Myocardial Perfusion MRI" proposed by Michael J-H et al. in the Journal of Magnetic Resonance Imaging 2004: 19:758-770 for a method of evaluating contrast-noise ratio (CNR) of the time-signal intensity curve. Quality of the time-signal intensity curve is deemed acceptable if the CNR thereof is equal to or greater than a predetermined threshold value. It is to be noted that the threshold value can be adjusted according to need. In the present embodiment, the threshold value is set to 30%.

In Step 4, an analyzing unit is used for acquiring a physical parameter set according to the time-signal intensity curve. The physical parameter set is related to type of disease and biological characteristics of the scanned area, and must include at least two physical parameters. For patients with leukemia, physical parameters related to blood flow need to be selected, and the physical parameters can be any two or all of the peak enhancement ratio (Peak), the permeability parameter (K trans), and the vascularity parameter amplitude (Amp). In the present embodiment, the physical parameter set includes the Peak, K trans, and Amp parameters.

The Peak is calculated for each ROI as $(SI_{max}-SI_{base})/SI_{base}$, is an indication of the concentration of contrast material in the intravascular and extravascular interstitial spaces, and represents the overall tissue perfusion. $SI_{max}$ is the maximum signal intensity of the time-signal intensity curve after injection of the contrast agent, whereas $SI_{base}$ is the signal intensity of the tissue before injection of the contrast agent, and is generally the average of the first few values of the time-signal intensity curve.

The Amp quantifies vascularity and leakage space, whereas the K trans is a measure of the permeability between intravascular and extravascular. The Amp and the K trans parameters are calculated quantitatively from the time-signal intensity curve according to the bi-compartmental model proposed by Brix et al. and Toft et al., and the calculation of which can be found in the following documents:

(1) Brix G, Semmler W, Port R, Schad L R, Layer G, Lorenz W J. "Pharmacokinetic Parameters in CNS Gd-DTPA Enhanced MR Imaging." J Comput Assist Tomogr 1991; 15:621-8.
(2) Tofts P S, Kermode A G. "Measurement of the Blood-Brain Barrier Permeability and Leakage Space Using dynamic MR Imaging. 1. Fundamental concepts." Magn Reson Med 1991; 17:357-67
(3) Tofts P S, Brix G, Buckley D L, et al. "Estimating Kinetic Parameters From Dynamic Contrast-Enhanced T(1)-Weighted MRI of a Diffusible Tracer: Standardized Quantities and Symbols." J Magn Reson Imaging 1999; 10:223-32.
(4) Paul S et al. "Modeling Tracer Kinetics in Dynamic Gd-DTPA MR Imaging." JMRI 1997; 7:91-101.
(5) Rujirutana Srikanchana et al. "A Comparison of Pharmacokinetic Models of Dynamic Contrast Enhanced MRI." 2004 IEEE proceedings of the $17^{th}$ IEEE symposium on computer-based medical systems.

In Step 5, Step 1 to Step 4 are repeated with different patients, one patient at a time, to obtain a plurality of physical parameter sets corresponding to the patients. It is to be noted that the same MRI scanner, configuration parameter set, and contrast agent are used during this step.

In Step 6, Step 1 to Step 5 are repeated with the MRI scanner configured according to a second configuration parameter set, which may be completely or partially different from the first configuration parameter set, such that another time-signal intensity curve with acceptable quality and another corresponding physical parameter set are generated for each of the patients. It is to be noted that model of the MRI scanner and type of the contrast agent may be changed at the beginning of this step.

In Step 7, a parameter significance-evaluating unit is used for performing univariate Cox regression analysis on the physical parameter sets of the patients with reference to prognoses (e.g., the overall survival rate and the disease-free survival rate) of the patients so as to evaluate significance of and obtain weight value of each of the physical parameters. Once the weight values are obtained, a risk score function, that is a sum of products of each of the physical parameters and the corresponding weight value, is obtained. A risk score of a patient calculated from the risk score function serves as the image biomarker for prognosis of the blood-related disease, such as acute myeloid leukemia. In this step, the commercial software package SAS ver 8.0 (SAS Institute, Cary, N.C., USA) is used for the analysis, and a detailed description of which can be found in the following documents:

(1) Wang T J, Gona P, Larson M G, et al. Multiple Biomarkers for the Prediction of First Major Cardiovascular Events and Death. N Engl J Med 2006; 355:2631-9.
(2) Chen H Y, Yu S L, Chen C H, et al. A Five-Gene Signature and Clinical Outcome in Non-Small-Cell Lung Cancer. N Engl J Med 2007; 356:11-20
(3) Lossos I S, Czerwinski D K, Alizadeh A A, et al. Prediction of Survival in Diffuse Large-B-Cell Lymphomas Based on the Expression of Six Genes. N Engl J Med 2004; 350:1828-1837.
(4) Beer D G, Kardia S L, Huang C C, et al. Gene-Expression Profiles Predict Survival of Patient with Lung Adenocarcinoma. Nat Med 2002; 8:816-824.

It is to be noted that a patient with a higher risk score is more exposed to risk of severity of the disease than a patient with a lower risk score. This is because the risk score takes into account a plurality of physical parameters, and hence is more comprehensive and credible than reliance upon a single physical parameter. In the present embodiment, the weights of the Amp, K trans, and Peak are 4.4, 40.7, and 1.7, respectively. Thus, the risk score function is:

$$\text{Risk score}=(4.4\times\text{Amp})+(40.7\times K\text{ trans})+(1.7\times\text{Peak})$$

Since the three parameters are related to tissue blood perfusion and permeability, the risk score can represent and is proportional to the rate of angiogenesis: a higher risk score indicates a higher severity of angiogenesis. The risk score will be elaborated in the section for clinical trial.

In Step 8, a computing unit is used for obtaining a risk score for each of the physical parameter sets of each of the patients according to the risk score function in Step 7.

In Step 9, the computing unit is further configured to acquire a mean of the risk scores computed in Step 8 so as to acquire a cutoff point for categorizing each of the patients into one of a high-risk group and a low-risk group. The patients in the high-risk group have prognoses worse than those of the patients in the low-risk group. That is to say, patients of the high-risk group have lower overall survival rates and disease-free survival rates.

It is to be noted and emphasized that, if different models of the MRI scanner, different configuration parameter sets, or different brands of the contrast agent are used in the training phase, the physical parameters of the first and second physical parameter sets will have different bases. However, the purpose of the training phase is to perform regression analysis and statistical computation on the two physical parameter sets of different bases with reference to clinical information of the patients, such that the image biomarkers (i.e., the risk scores) and the cutoff point are not influenced by the above-mentioned differences and have a common basis. Therefore, regardless of the differences between the first and second configuration parameter sets, as long as the contrast-to-noise ratio (CNR) (i.e., quality) of the time-signal intensity curves is equal to or greater than the predetermined threshold value, the risk scores thus obtained can be compared to the cutoff point. The method of prognosis of a blood-related disease proposed in this invention can therefore be widely adopted by most medical institutes.

Application Phase:

The purpose of the application phase is to use the image biomarker obtained in the training phase for prognosis of a blood-related disease, such as acute myeloid leukemia.

Figure 3:
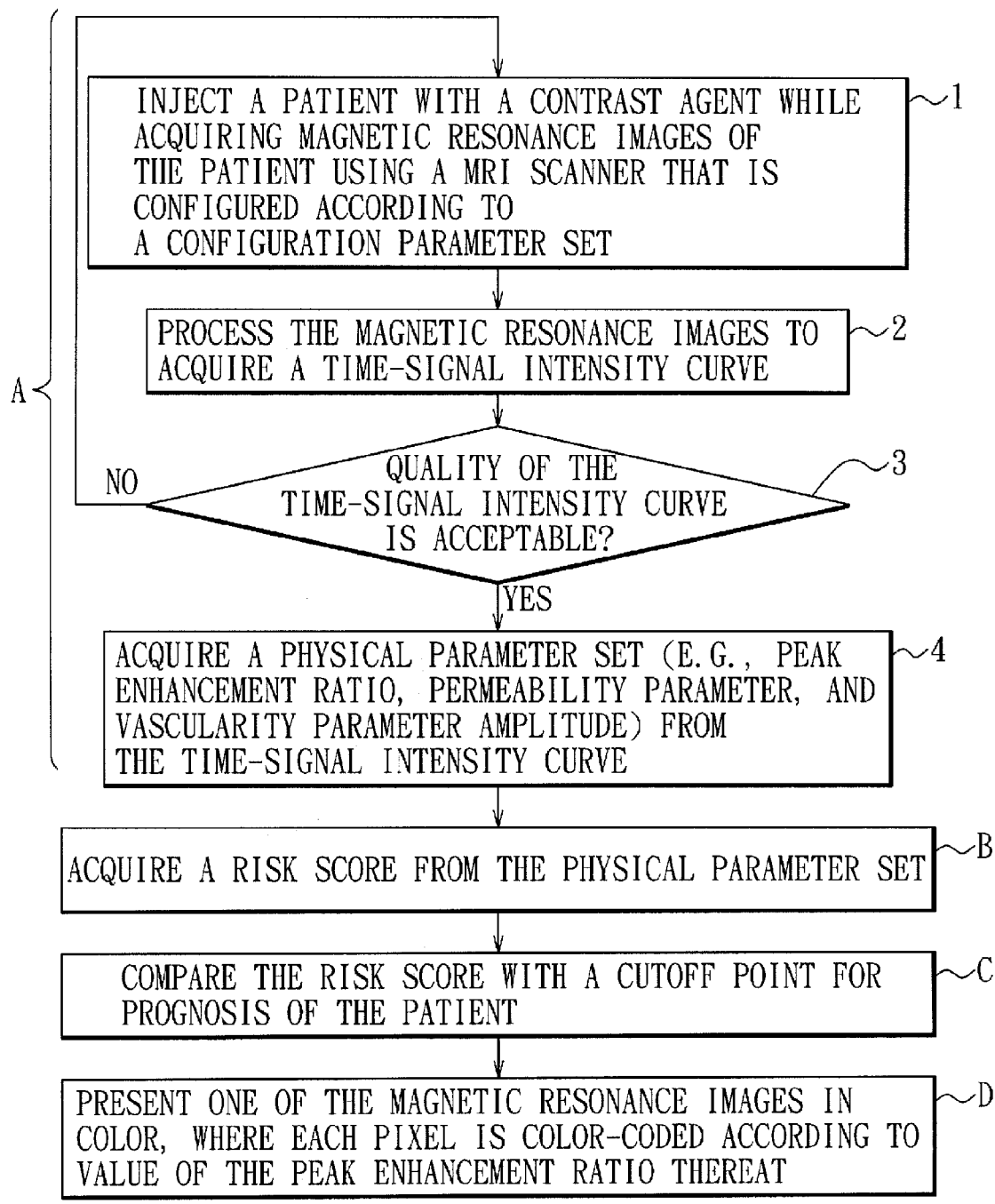
FIG. 3 is a flow chart illustrating the preferred embodiment of a method of the present invention suitable for prognosis of a blood-related disease.

Referring to FIG. 3, a patient who is suspected of having, or is undertaking chemotherapy for, the blood-related disease can undertake the application phase for prognosis. The steps of the application phase are non-invasive, bring comparatively less pain to the patients, and hence can be performed repeatedly within a short duration of time. Thus, it is possible to monitor and predict effect of the treatment, thereby determining whether the treatment should be continued or course of the treatment should be changed. If the risk score is high and indicates poor prognosis for the patient receiving conventional induction chemotherapy, the patient can be advised to undertake other treatments such as anti-angiogenesis target therapy. The application phase includes four steps.

In Step A, Step 1 to Step 4 of the training phase are performed to obtain a physical parameter set of the patient. It is noted that any one of the contrast agent, model of the MRI scanner, and the configuration parameter set used in the application phase may be different from those used in the training phase. However, if the same contrast agent, model of the MRI scanner, and configuration parameter set are used, Step 4 of the training phase can be omitted.

In Step B, the computing unit is used to compute the risk score of the patient according to the risk score function established in Step 8 of the training phase.

In Step C, a risk-evaluating unit is used to compare the risk score with the cutoff point obtained in Step 10 of the training phase so as to categorize the patient into one of the high- and low-risk groups, and perform prognosis of the disease therefrom.

The application phase may further include Step D.

Figure 4:
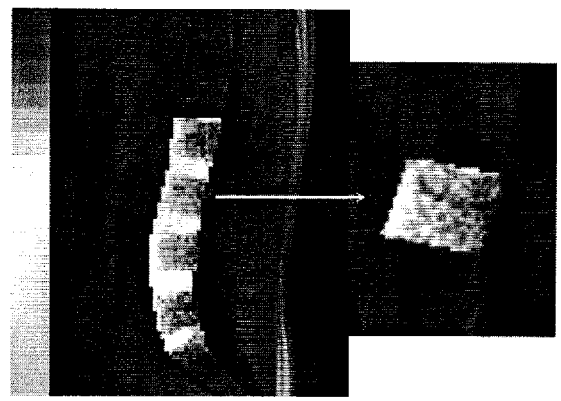
FIG. 4 is a screenshot of an image obtained as a result of color coding a magnetic resonance (MR) image according to peak enhancement ratio (Peak) values.

In Step D, referring to FIG. 4, a color-mapping unit is used to analyze and color-code one of the images in the MR image set, and then present said one of the images in color on a medium (e.g., a monitor). Each pixel of said one of the images is color-coded according to value of the Peak, which is analyzed in Step 5 of the training procedure, thereat. For example, pixels with Peak values in the high, medium, and low ranges are presented as red, yellow, and green, respectively. The number of ranges of Peak values and corresponding number of colors can be changed according to need. Preferably, among the MR image set, the image with the highest Peak value in the region of interest is converted and presented in color. The purpose of this step is that grayscale images are less distinguishable to human eyes compared to color images. The color-coding map is designed according to the Peak values because the Peak value has been proven to be the independent prognostic predictor by using the multivariate Cox proportional hazard regression analysis.

Figure 5:
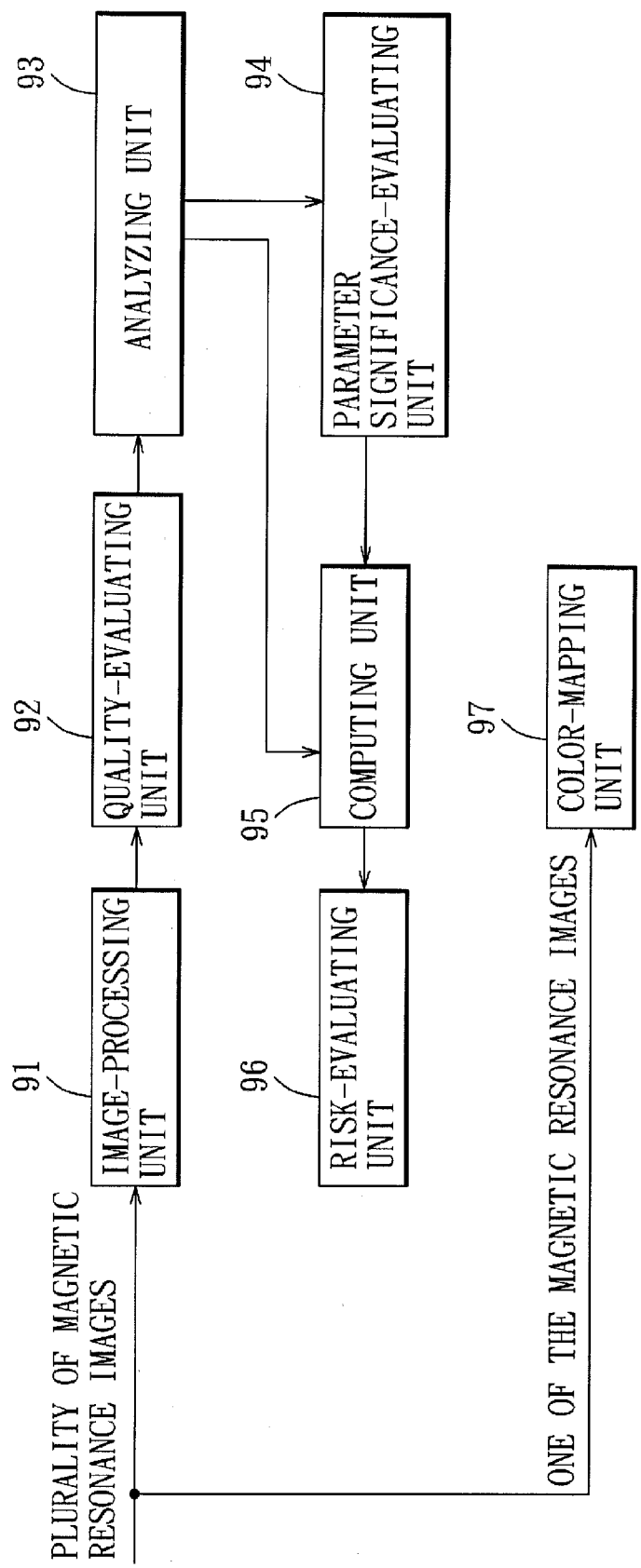
FIG. 5 is a functional block diagram of an apparatus of the present invention for prognosis of a blood-related disease.

Referring to FIG. 5, the image-processing unit 91, quality-evaluating unit 92, analyzing unit 93, parameter significance-evaluating unit 94, computing unit 95, risk-evaluating unit 96, and color-mapping unit 97 can be implemented by either software or hardware.

If implemented by hardware, the above-mentioned units cooperate to form an automated device for prognosis of the blood-related disease. In the device:

the image-processing unit 91 receives a plurality of MR images, processes the MR images to generate a time-signal intensity curve, and is coupled to the quality-evaluating unit 92 for providing the time-signal intensity curve thereto;

the quality-evaluating unit 92 evaluates quality of the time-signal intensity curve according to a predetermined threshold value, is coupled to the analyzing unit 93, and provides the time-signal intensity curve with acceptable quality to the analyzing unit 93;

the analyzing unit 93 acquires a physical parameter set from the time-signal intensity curve, and is coupled to the parameter significance-evaluating unit 94 and the computing unit 95 for providing the physical parameter set thereto;

the parameter significance-evaluating unit 94 evaluates weights of physical parameters of the physical parameter set, generates a risk score function, and is coupled to the computing unit 95;

the computing unit 95 generates a risk score according to the risk score function and the physical parameters of the physical parameter set, and is coupled to the risk-evaluating unit 96;

the risk-evaluating unit 96 compares the risk score with a predetermined cutoff point so as to categorize the patient into one of a high-risk group and a low-risk group; and the color-mapping unit 97 receives and color-maps one of the MRI images.

The aforesaid device can be a standalone device or integrated into a conventional MRI scanner.

When implemented by software, the above-mentioned units can be implemented by software modules that collectively form a software program product, and the software program product can be executed by a hardware device with processing ability (i.e., a computer).

Preferably, the method of the present invention is suitable for prognosis of bone marrow-related diseases. More preferably, the method of the present invention is particularly suitable for prognosis of patients who have just been diagnosed with or are suspected of having acute myeloid leukemia (AML). The clinical trial and observation will be described hereinafter.

Table 1 lists brands, concentrations, dosages, and injection methods of the contrast agent used in the training and application phases. It is to be noted that rate of blood flow is now taken into consideration, and that the brief injection rate of contrast agent is set to 2.0 ml per second.

TABLE 1

| | Training phase | | |
|---|---|---|---|
| | First run of Step 1 to Step 6 to obtain first physical parameter sets (using first configuration parameter set) | Second run of Step 1 to Step 6 to obtain second physical parameter sets (using second configuration parameter set) | Application phase |
| Number of patients | 78 | 17 | The same as those of first run of training phase |
| Brand, concentration, and dosage of contrast agent | Brand: Omniscan (GE Health Ireland, Ireland) Concentration: 0.5 mmol/ml Dosage: 0.15 mmol/kg | Brand: Magnevist (Bayer-Schering, Berlin, Germany) Concentration: 0.5 mmol/ml Dosage: 0.1 mmol/kg | |
| Injection method | Injection at a brief injection rate of 2.0 ml/s by power injector via 21-gauge intravenous catheter injected into antecubital vein of right elbow, and then followed by normal saline flash | | |

Table 2 lists models of MRI scanners and configuration parameter sets used in the training and application phases. Two models of MRI scanners made by Siemens were used in the training phase, and several configuration parameters of the two MRI scanners differ from each other. Furthermore, the same MRI scanner and configuration parameter set were used for obtaining the first physical parameter sets and in the application phase. It is also noted that the pulse sequence used was the fast low-grade shot gradient-echo sequence, and the acquisition rate was designed according to amount and rate of blood flow of vertebral bone marrow.

TABLE 2

| | Training phase | | |
|---|---|---|---|
| | First run of Step 1 to Step 6 to obtain first physical parameter sets (using first configuration parameter set) | Second run of Step 1 to Step 6 to obtain second physical parameter sets (using second configuration parameter set) | Application phase |
| Model | 1.5 Tesla superconducting system (Sonata by Siemens, Erlangen, Germany) | 1.5 Tesla superconducting system (Magnetom Vision Plus by Siemens, Erlangen, Germany) | The same as those of first run of training phase |
| Scanned part | Lumbar spine (covered from T11 to S1 vertebrae) | | |
| Slice thickness | 10 mm | | |
| Field of view | 28 cm | | |
| Pulse sequence | Fast low-grade shot gradient-echo sequence | | |
| Repetition time | 500 ms | 8.5 ms | |
| Echo time | 1.37 ms | 4.0 ms | |
| Pre-pulse inversion time | 230 ms | 160 ms | |
| Flip angle | 8 degrees | 10 degrees | |
| Acquisition matrix | 157 × 256 | 72 × 128 | |
| Average of excitation | 4 | 2 | |
| Acquisition rate | Every 2 seconds | Every 1 second | |
| Acquisition time | 600 seconds | 100 seconds | |

For the clinical trial, the preset threshold value for the CNR of the time-signal intensity curves is 30%. In order to improve accuracy of the physical parameter sets, three regions of interests (ROIs) were chosen, which were the second, third, and fourth lumbar vertebrae. The physical parameter sets of the three ROIs were obtained in Step 5 and then averaged to generate another physical parameter set with higher accuracy and comprehensiveness. The physical parameters chosen were the Amp, the K trans, and the Peak, and the weights thereof were 4.4, 40.7, and 1.7, respectively. Accordingly, the risk score function of the present embodiment is: Risk score= $(4.4 \times Amp)+(40.7 \times K\ trans)+(1.7 \times Peak)$. The cutoff point of the risk score was 3.546.

In the following part of the application phase, conditions of the patients at initial diagnosis of acute myeloid leukemia were evaluated using the risk scores and the cutoff point.

Figure 6A:
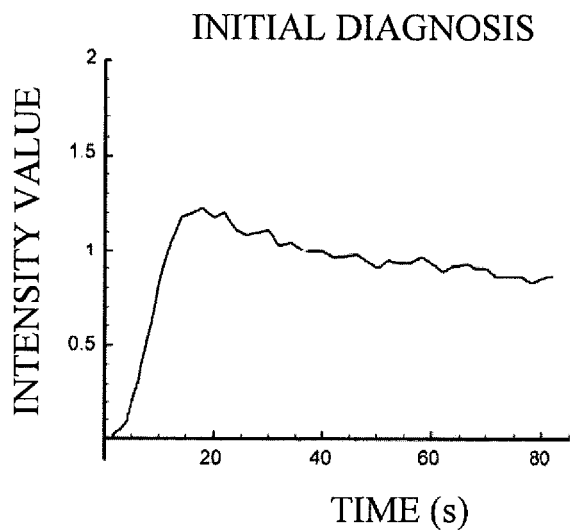
FIGS. 6($a$) and 6($b$) are a time-signal intensity curve and a corresponding color-coded angiogenesis map of a patient at initial diagnosis, respectively.
Figure 6B:
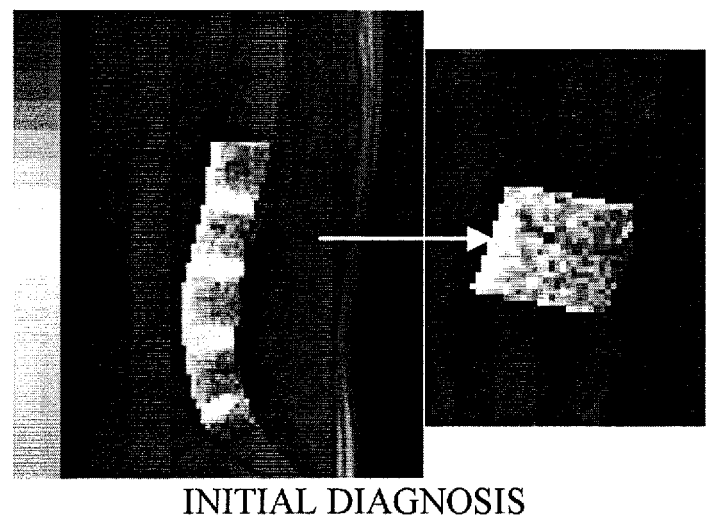
Figure 7A:
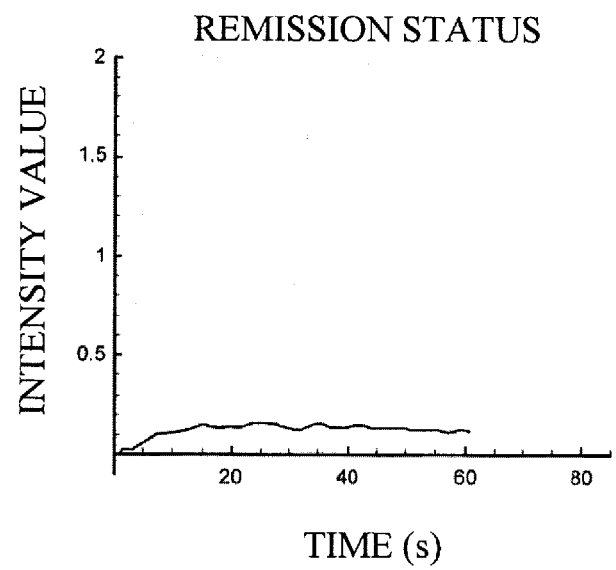
FIGS. 7($a$) and 7($b$) are a time-signal intensity curve and a corresponding color-coded angiogenesis map of the patient at remission status, respectively.
Figure 7B:
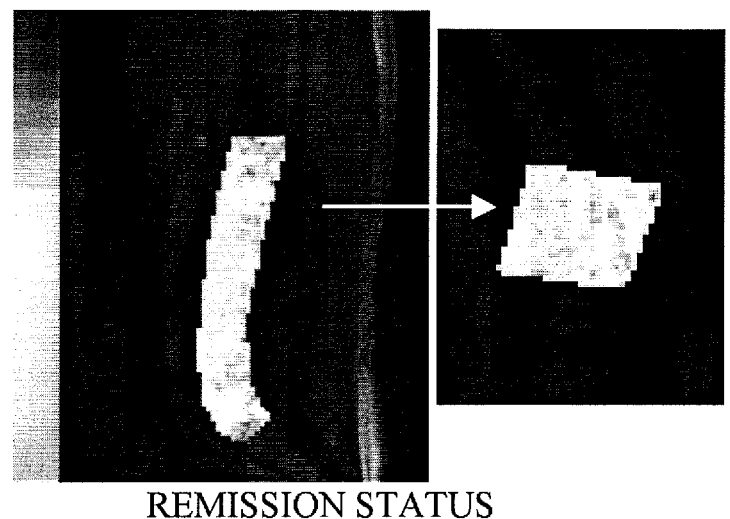

FIGS. 6(a) and 6(b) are a time-signal intensity curve and a corresponding color-coded angiogenesis map of one of the patients at initial diagnosis, respectively. FIGS. 7(a) and 7(b) are a time-signal intensity curve and a corresponding color-coded angiogenesis map of said one of the patients at remission status, respectively. It can be noted that said one of the patients had a higher blood perfusion (i.e., higher angiogenesis) at initial diagnosis, and a lower blood perfusion (i.e., lower angiogenesis) at remission status. Comparing FIGS. 6(b) and 7(b), the decrease in angiogenesis is indicated by the change in color (from red to yellow).

Figure 8A:
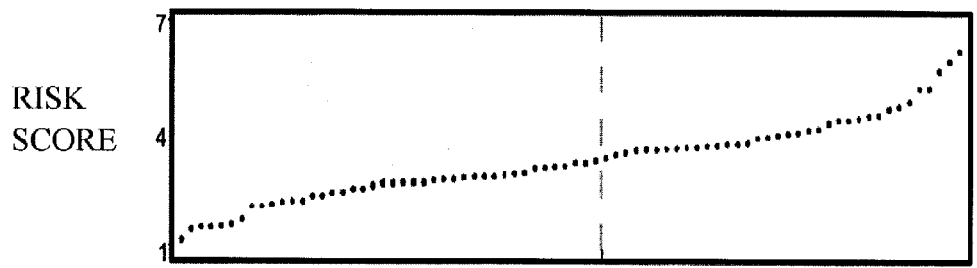
FIG. 8($a$) is a plot of risk scores of 78 patients at initial diagnosis.
Figure 8B:
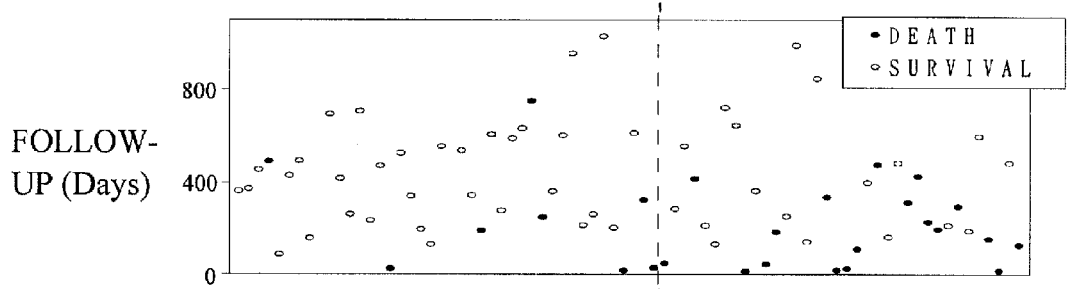
Figure 8C:
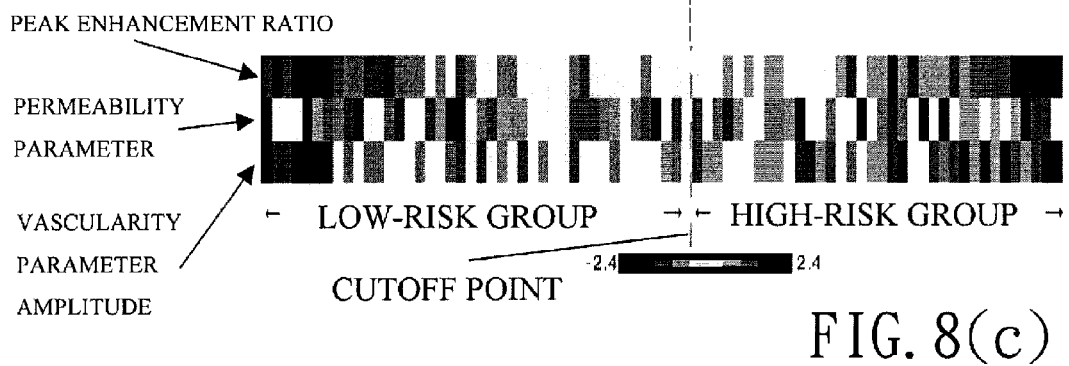

FIG. 8(a) shows a plot of the risk scores of the 78 patients arranged from low to high. FIG. 8(b) shows the post-treatment survival statuses of the patients during the follow-up. FIG. 8(c) shows the intensities of physical parameters of the patients. The dashed-line marked vertically across FIGS. 8(a) to 8(c) is the cutoff point for dividing the patients into one of a high-risk group and a low-risk group. There were 36 patients and 42 patients in the high- and low risk groups, respectively. As can be observed from FIGS. 8(a) to 8(c), the patients of the high-risk group have a relatively higher proportion of death.

Clinically, a conventional method for observation of bone marrow angiogenesis employs bone marrow biopsy and special immuno-histo-chemical staining with detailed but time-consuming counting of its microvessel density (MVD), and hence is less effective. In comparison, the present invention permits acquisition of risk score of bone marrow angiogenesis by non-invasive MRI scanning. The prognoses thus obtained were verified with numbers of days the patients survived.

Figure 9A:
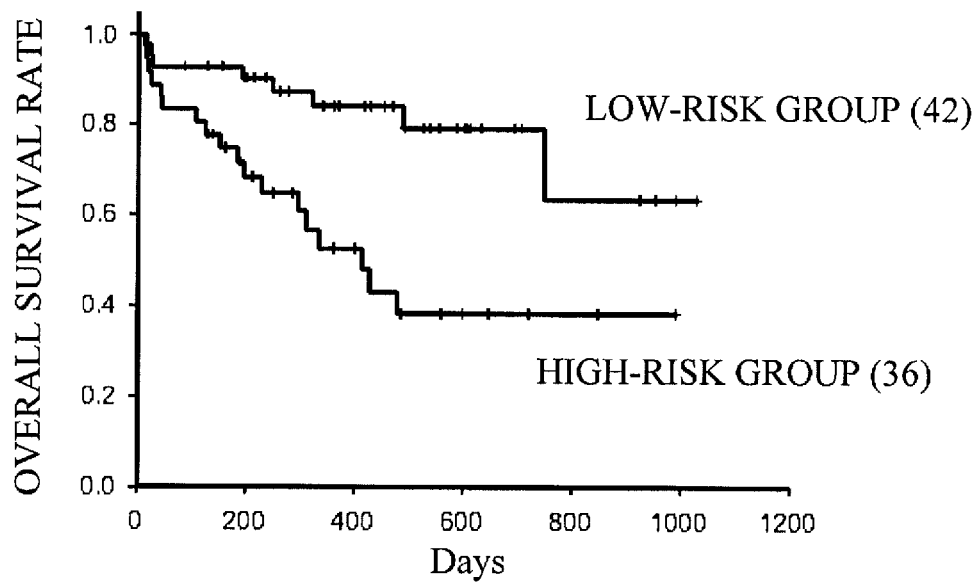
FIG. 9($a$) shows plots of overall survival of each of a high-risk group and a low-risk group.
Figure 9B:
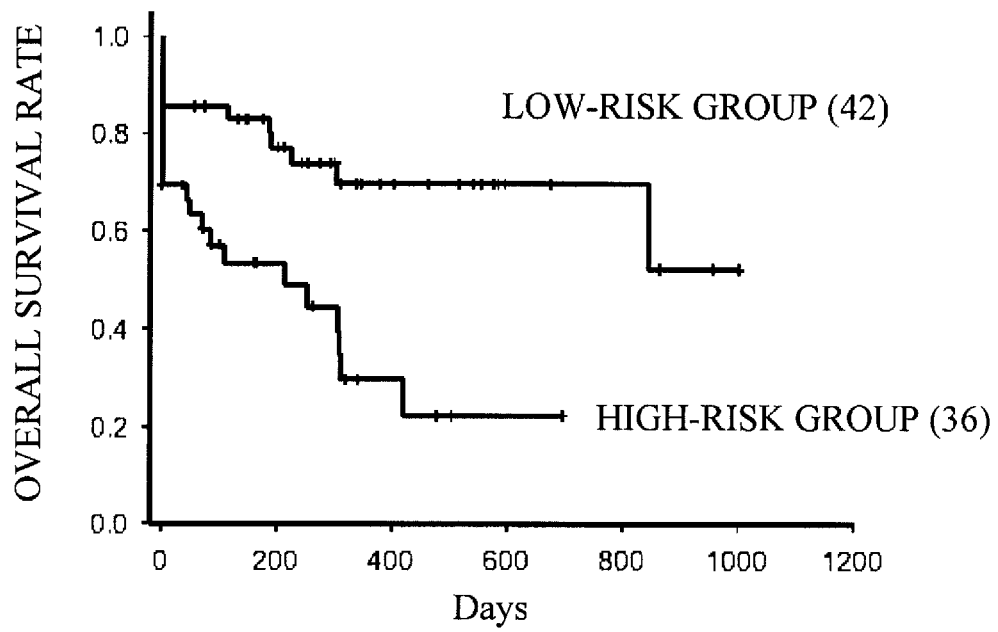

FIG. 9(a) shows plots of overall survival rate for the high- and low-risk groups obtained using the conventional Kaplan-Meiere method. FIG. 9(b) is similar to FIG. 9(a), but shows plots of disease-free survival instead of the overall survival. It can be distinctly observed from FIGS. 9(a) and 9(b) that the high-risk group had lower rates of overall survival and disease-free survival. The overall survival was measured from the date of first diagnosis to the date of last follow-up or death from any cause, whereas the disease-free survival indicates that the patient had achieved complete remission and had not relapsed by the end of the clinical trial.

Figure 10A:
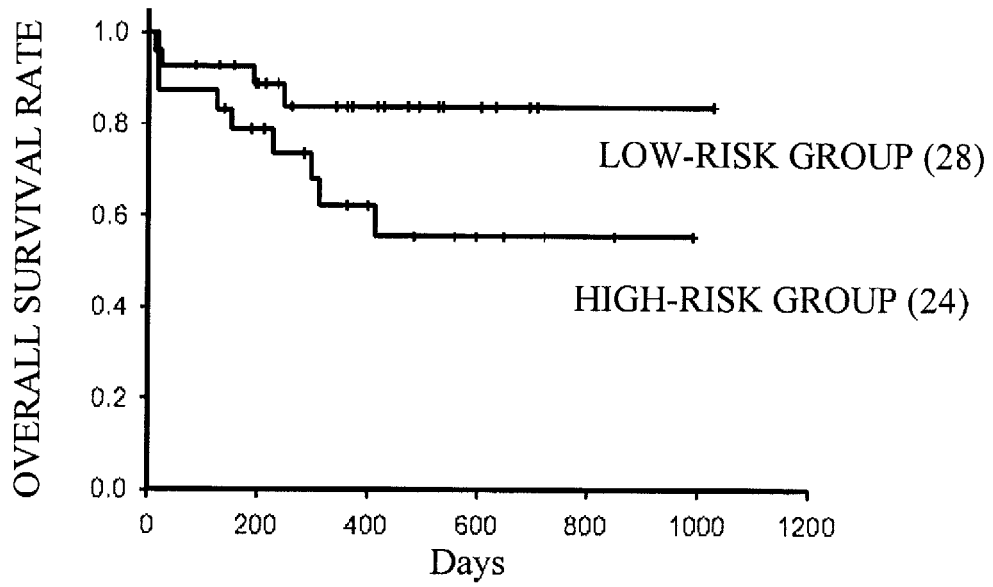
FIGS. 10($a$) and 10($b$) are similar to FIGS. 9($a$) and 9($b$), but only analyzes those (52) among the 78 patients who had intermediate-risk cytogenetics.
Figure 10B:
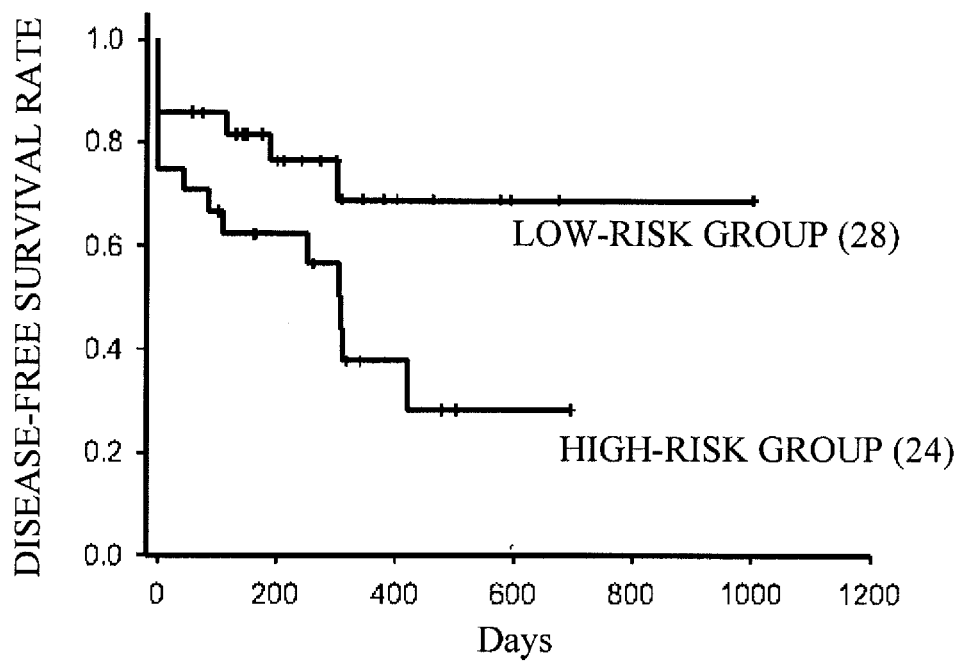

FIGS. 10(a) and 10(b) are similar to FIGS. 9(a) and 9(b), but only include results of those of the 78 patients who were diagnosed with intermediate-risk cytogenetics. There were 52 patients with intermediate-risk cytogenetics: 24 were in the high-risk group, and 28 were in the low-risk group. According to previous studies, patients with high-risk cytogenetics have poor prognoses, patients with low-risk cytogenetics have better prognoses, and patients with intermediate-risk cytogenetics have unknown prognoses. It is to be noted that, generally, 70% of patients have intermediate-risk cytogenetics, and hence prognoses of the majority of patients cannot be obtained from the cytogenetics. Referring to FIGS. 10(a) and 10(b), the plots of overall survival and disease-free survival obtained for the 52 patients with intermediate-risk cytogenetics are similar to those of FIGS. 9(a) and 9(b). Therefore, the present invention is suitable for prognoses of patients with intermediate-risk cytogenetics.

In addition, evaluation of whether the risk score can be an independent predictor was performed using the multivariate Cox proportional hazard regression analysis of the SAS software version 9.1 (SAS Institute, Cary, N.C., USA). The result indicated that the risk score is an independent predictor, the hazard ratio was 6.1, the 95% confidence interval was 2.39-15.82, and the probability was 0.0002. A hazard ratio of 6.1 means that the overall survival rate is reduced by six times with every increment of one in the risk score.

Moreover, relations of each of the physical parameters used in the application phase and a respective one of the overall survival and the disease-free survival were analyzed. The CART analysis was performed to obtain a corresponding cutoff point for each of the relations, and each of the cutoff points was used for categorizing patients into one of a high-risk group and a low-risk group.

Figure 11:
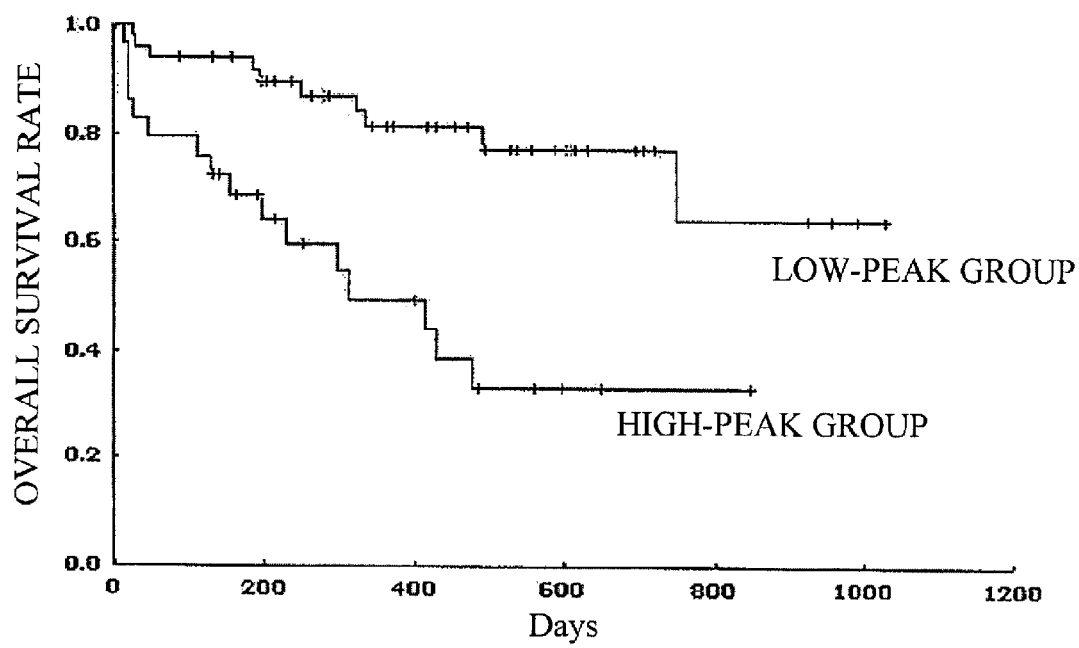
FIG. 11 is a plot of overall survival of each of a high-Peak group and a low-Peak group.
Figure 12:
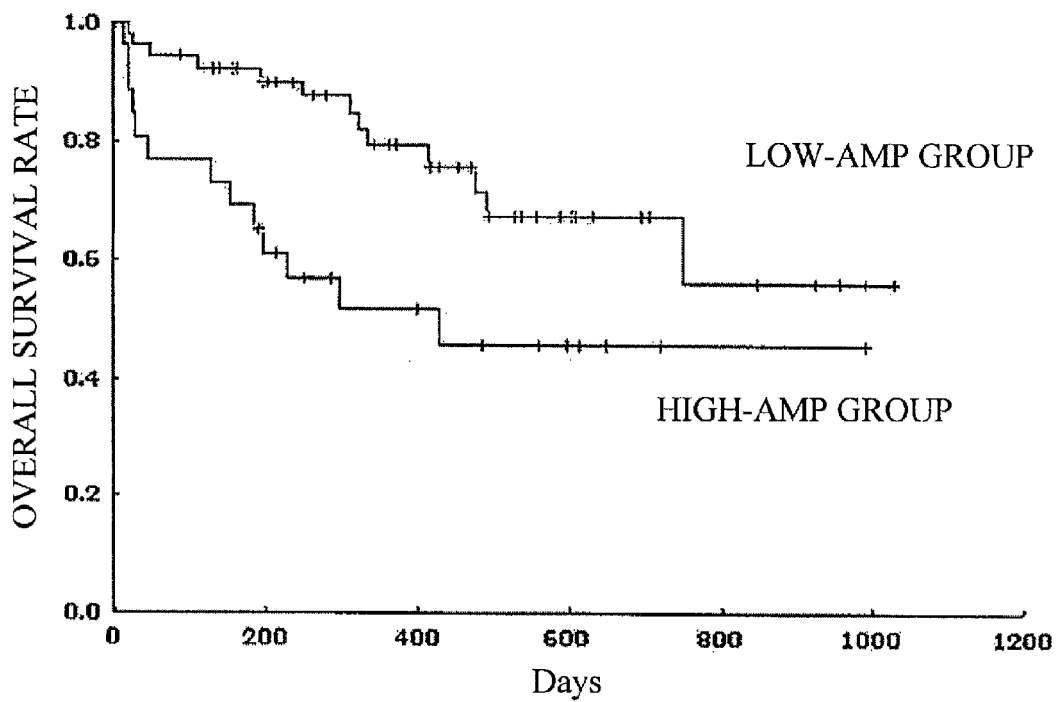
FIG. 12 is a plot of overall survival of each of a high-Amp group and a low-Amp group.
Figure 13:
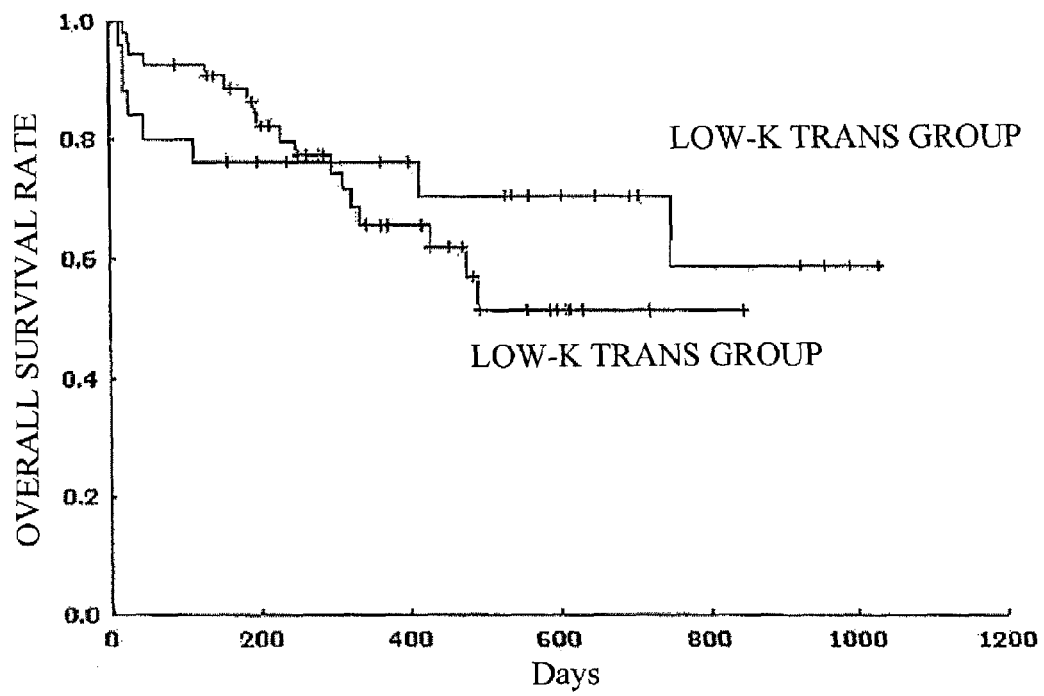
FIG. 13 is a plot of overall survival of each of a high-K trans group and a low-K trans group.
Figure 14:
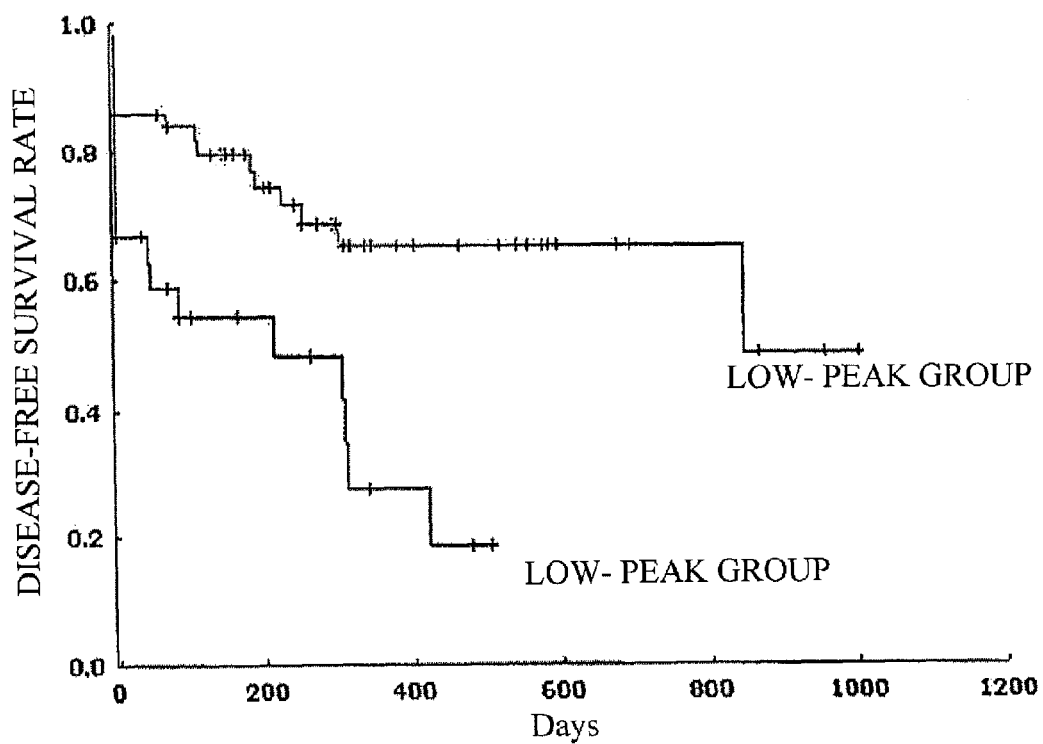
FIG. 14 is a plot of disease-free survival of each of a high-Peak group and a low-Peak group.
Figure 15:
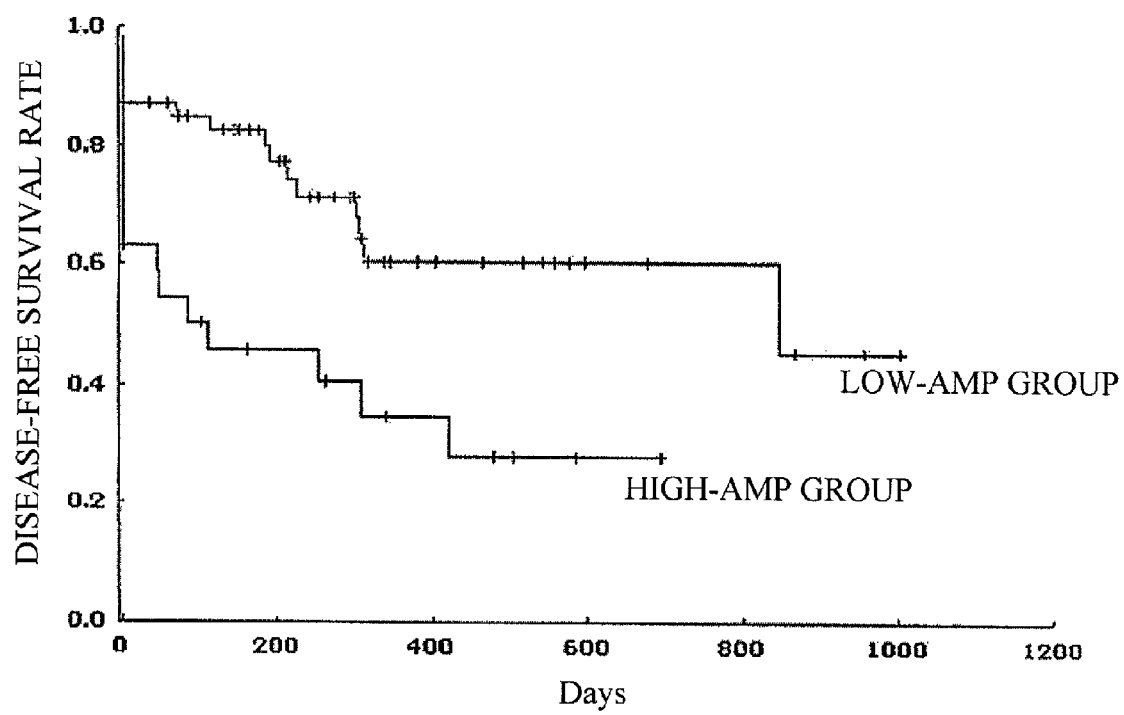
FIG. 15 is a plot of disease-free survival of each of a high-Amp group and a low-Amp group.
Figure 16:
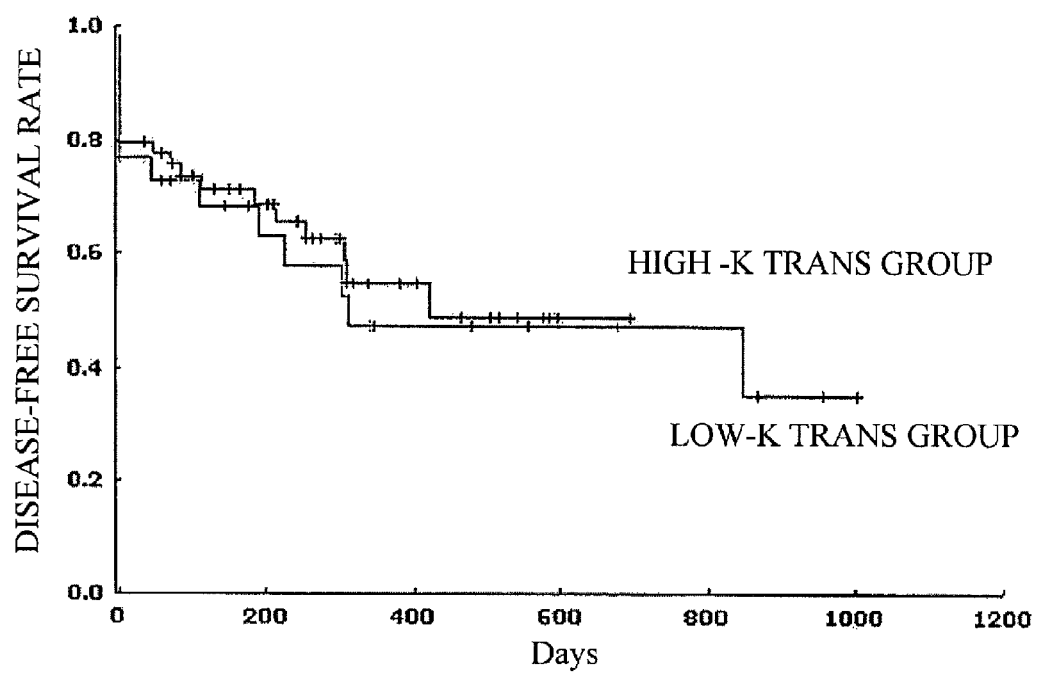
FIG. 16 is a plot of disease-free survival of each of a high-K trans group and a low-K trans group.

FIGS. 11, 12, and 13 show the relations of the Peak, the Amp, and the K trans with the overall survival, respectively. It can be noted that the overall survival curves of each of the Peak and the Amp are similar to those of the risk score, whereas the overall survival curves of the K trans are comparatively different. FIGS. 14, 15, and 16 show the relations of the Peak, the Amp, and the K trans with the disease-free survival, respectively. It can also be noted that the K trans is the only parameter that shows substantially different curves. These findings indicate that a single physical parameter may be used to represent a portion of biological characteristics of an observed area, but may not be used to represent the overall angiogenesis. The risk score of the present invention incorporates multiple physical parameters, and hence is more comprehensive than a single physical parameter. Moreover, the risk score is not affected or limited by model of the MRI scanner, values of the configuration parameters, and brand of the contrast agent.

It is to be noted that, although MRI scanners of different models of the same manufacturer were used in the clinical trial, MRI scanners available from different manufacturers may be used in actual applications, as long as the quality requirement of the time-signal intensity curve is met.

In summary, the training phase eliminates differences in model and maker of the MRI scanner, configuration parameter set, and type of the contrast agent, and then generates a risk score function. A risk score obtained from the risk score function serves as an image biomarker suitable for prognosis of a blood-related disease, such as acute myeloid leukemia. In the application phase, patients with risk scores higher than the cutoff point have poorer overall survival rate and disease-free survival rate compared to those with risk scores lower than the cutoff point. The present invention can be implemented by software or hardware, and can be integrated into a MRI scanner. The prognosis can be presented with a color-mapped MR image. The risk score function and the cutoff point of the present invention can also be used for prognosis of a patient with intermediate-risk cytogenetics.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method of acquiring an image biomarker suitable for prognosis of a blood related disease, comprising the steps of:
    a) using an analyzing unit to acquire physical parameter sets, each including at least two physical parameters comprising a peak enhancement ratio, an initial maximum enhancement slope, a permeability parameter, and a vascularity parameter amplitude, respectively from at least two sets of time-signal intensity curve, each set of the time-signal intensity curve being respectively obtained from magnetic resonance image sets of different subjects that are diagnosed as having the blood-related disease, each of the magnetic resonance image sets being acquired by using one of first and second contrast agents, and by using one of first and second magnetic resonance imaging (MRI) scanners which is configured respectively by using one of first and second configuration parameter sets, wherein the first contrast agent(s) to be used is different from the second contrast agent(s) to be used, the first scanner to be used is different from the second scanner to be used, and the first configuration parameter set to be used is different from the second configuration parameter set to be used;
    b) using a parameter significance-evaluating unit to analyze the physical parameter sets thus acquired with reference to prognoses of the different subjects so as to evaluate significance of each of the physical parameters and obtain weight values corresponding to the physical parameters; and
    c) configuring a computing unit to establish a risk score function that is a sum of products of each of the physical parameters and the corresponding weight value, wherein a risk score obtained using the risk score function serves as the image biomarker suitable for prognosis of the blood-related disease, wherein the risk score function is:

risk score=(4.4×vascularity parameter amplitude)+(40.7×permeability parameter)+(1.7×peak enhancement ratio).

2. The method as claimed in claim 1, further comprising the steps of:
    d) using the computing unit to compute the risk scores of the different subjects based on the risk score function and the physical parameter sets acquired by the analyzing unit, and to obtain an average of the risk scores computed thereby so as to acquire a cutoff point suitable for categorizing each of the subjects into one of a high-risk group and a low-risk group.

3. The method as claimed in claim 1, wherein the time-signal intensity curves from which the physical parameter sets are acquired have a contrast-to-noise ratio greater than a preset threshold value.

4. The method as claimed in claim 1, wherein the parameter significance evaluating unit employs univariate cox regression to acquire the weight value of each of the physical parameters.

5. The method as claimed in claim 1, wherein the physical parameters of the physical parameter sets include a peak enhancement ratio and a permeability parameter.

6. The method as claimed in claim 5, wherein the physical parameters of the physical parameter sets further include a vascularity parameter amplitude.

7. The method as claimed in claim 1, wherein the blood-related disease is myeloid disease.

8. The method as claimed in claim 7, wherein the blood-related disease is acute myeloid leukemia.

9. The method as claimed in claim 1, further comprising, prior to step a),
    using a MRI scanner to scan the subjects so as to acquire the magnetic resonance image sets,
    using an image-processing unit to process the magnetic resonance image sets so as to obtain the time-signal intensity curves, and
    using a quality evaluating unit to evaluate the quality of the time-signal intensity curves,
    wherein the analyzing unit acquires the physical parameter sets form the time-signal intensity curves with acceptable quality, and
    wherein the time-signal intensity curves with non-acceptable quality are discarded in favor of the time-signal intensity curves obtained from the magnetic resonance image sets acquired using an adjusted configuration parameter set of the MRI scanner.

10. The method as claimed in claim 9, wherein the quality of the time-signal intensity curves is deemed acceptable if a contrast-to-noise ratio thereof is greater than a preset threshold value.

11. A method of prognosis of a blood-related disease, comprising the steps of:
    i) using an analyzing unit to acquire a physical parameter set, that includes at least two physical parameters comprising a peak enhancement ratio, an initial maximum enhancement slope, a permeability parameter, and a vascularity parameter amplitude, from a time-signal intensity curve, the time-signal intensity curve being obtained from a magnetic resonance image set of a patient suspected of having the blood-related disease;
    ii) using a computing unit to compute a risk score of the patient based on a risk score function established in the computing unit and the physical parameters acquired by the analyzing unit, the risk score function being a sum of products of each of the physical parameters and a weight value corresponding thereto, wherein the risk score obtained using the risk score function serves as an image biomarker suitable for prognosis of the blood-related disease, and where in the risk score function established in the computing unit is:

risk score=(4.4×vascularity parameter amplitude)+(40.7×permeability parameter)+(1.7×peak enhancement ratio); and iii) using a risk-evaluating unit to evaluate and predict a condition of the patient based on the computed risk score.

12. The method as claimed in claim 11, wherein in step i) the physical parameters of the physical parameter set includes a peak enhancement ratio, and step iii) includes:
    using a color mapping unit to analyze one of the images in the MRI image set, and to set different colors for different values of the peak enhancement ratio of said one of the images.

13. The method as claimed in claim 11, wherein the time-signal intensity curve from which the physical parameter set is acquired has a contrast-to-noise ratio greater than a present threshold value.

14. The method as claimed in claim 11, wherein the physical parameters of the physical parameter set include a peak enhancement ratio, a vascularity parameter amplitude, and a permeability parameter.

15. The method as claimed in claim 11, wherein the risk-evaluating unit compares the risk score of the patient with a predetermined cutoff point, and the patient is categorized into a high-risk group if the risk score is higher than the cutoff point, and into a low-risk group if otherwise.

16. The method as claimed in claim 11, wherein the blood-related disease is acute myeloid leukemia.

17. The method as claimed in claim 11, further comprising, prior to step i),
using a magnetic resonance imaging (MRI) scanner to scan the patient so as to acquire the magnetic resonance image set,
using an image-processing unit to process the magnetic resonance image set so as to obtain the time-signal intensity curve, and
using a quality evaluating unit to evaluate the quality of the time-signal intensity curve,
wherein the analyzing unit acquires the physical parameter set from the time-signal intensity curve with acceptable quality, and
wherein the time-signal intensity curve with non-acceptable quality is discarded in favor of the time-signal intensity curve obtained from the magnetic resonance image set acquired using an adjusted configuration parameter set of the MRI scanner.

18. An apparatus for prognosis of a blood-related disease, said apparatus being adapted to process a magnetic resonance image set of a patient acquired using a magnetic resonance imaging (MRI) scanner and comprising:
an image processing unit for processing the magnetic resonance image set to obtain a time-signal intensity curve;
an analyzing unit for acquiring a physical parameter set, that includes at least two physical parameters comprising a peak enhancement ratio, an initial maximum enhancement slope, a permeability parameter, and a vascularity parameter amplitude, from the time-signal intensity curve obtained by said image processing unit;
a computing unit for computing a risk score of the patient based on a risk score function established in said computing unit and the physical parameters acquired by said analyzing unit, the risk score function being a sum of products of each of the physical parameters and a weight value corresponding thereto, wherein the risk score obtained using the risk score function serves as an image biomarker suitable for prognosis of the blood-related disease, and wherein the risk score function established in said computing unit is:

risk score=(4.4×vascularity parameter amplitude)+ (40.7×permeability parameter)+(1.7×peak enhancement ratio); and a risk-evaluating unit for evaluating and predicting a condition of the patient based on the risk score computed by said computing unit.

19. A computer program product comprising a non-transitory machine-readable storage medium that comprises program instructions for causing a computer to perform consecutive steps of a method of prognosis of a blood-related disease, said program instructions comprising:
a first code for configuring the computer to receive and process a magnetic resonance image set of a patient acquired using a magnetic resonance imaging (MRI) scanner to obtain a time-signal intensity curve;
a second code for configuring the computer to acquire a physical parameter set, that includes at least two physical parameters comprising a peak enhancement ratio, an initial maximum enhancement slope, a permeability parameter, and a vascularity parameter amplitude, from the time-signal intensity curve;
a third code for configuring the computer to compute a risk score of the patient based on a pre-established risk score function and the physical parameters acquired from the time-signal intensity curve, the risk score function being a sum of products of each of the physical parameters and a weight value corresponding thereto, wherein the risk score obtained using the pre-established risk score function serves as an image biomarker suitable for prognosis of the blood-related disease, and wherein the pre-established risk score function is:

risk score=(4.4×vascularity parameter amplitude)+ (40.7×permeability parameter)+(1.7×peak enhancement ratio); and a fourth code for configuring the computer to evaluate and predict a condition of the patient based on the computed risk score.

* * * * *